United States Patent
Schmitt et al.

(10) Patent No.: US 10,823,804 B2
(45) Date of Patent: Nov. 3, 2020

(54) MAGNETIC RESONANCE METHOD AND APPARATUS FOR IMAGING MOVING LIQUID IN A SUBJECT

(71) Applicant: Siemens Healthcare GmbH, Erlangen (DE)

(72) Inventors: Peter Schmitt, Weisendorf (DE); Peter Speier, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 154 days.

(21) Appl. No.: 16/034,736

(22) Filed: Jul. 13, 2018

(65) Prior Publication Data

US 2019/0018098 A1    Jan. 17, 2019

(30) Foreign Application Priority Data

Jul. 13, 2017    (EP) .................................. 17181239

(51) Int. Cl.
*G01R 33/561*      (2006.01)
*A61B 5/026*      (2006.01)
*G01R 33/56*      (2006.01)
*G01R 33/563*      (2006.01)
*G01R 33/48*      (2006.01)

(52) U.S. Cl.
CPC ........ *G01R 33/5614* (2013.01); *A61B 5/0263* (2013.01); *G01R 33/563* (2013.01); *G01R 33/5607* (2013.01); *G01R 33/5635* (2013.01); *G01R 33/4822* (2013.01)

(58) Field of Classification Search
CPC ............ G01R 33/5614; G01R 33/5607; G01R 33/563; G01R 33/5635; G01R 33/4822; A61B 5/0263
See application file for complete search history.

(56) References Cited

U.S. PATENT DOCUMENTS

| | | | |
|---|---|---|---|
| 5,070,299 A * | 12/1991 | Kiefer | G01R 33/482 324/309 |
| 5,307,014 A | 4/1994 | Laub | |
| 2017/0307714 A1 * | 10/2017 | Okell | G01R 33/56366 |

OTHER PUBLICATIONS

Wang et al., "Improved Tensor Based Registration: An Heterogeneous Approach". (Year: 2012).*
Nägele, et al. "The Effects of Linearly Increasing Flip Angles on 3D Inflow MR Angiography" Magnetic Resonance in Medicine, vol. 31, No. 5, p. 561-566; (1994).

(Continued)

*Primary Examiner* — Tung X Nguyen
*Assistant Examiner* — Feba Pothen
(74) *Attorney, Agent, or Firm* — Schiff Hardin LLP

(57) ABSTRACT

In a method and apparatus for capturing magnetic resonance data from an imaging volume of a patient in which liquid, such as particular blood, is moving, a bSSFP magnetic resonance sequence is executed in which nuclear spins located within the imaging volume are cyclically excited by radiation of a radio-frequency pulse, using a magnetic resonance scanner. A ramp pulse is used as the radio-frequency pulse, which establishes a flip angle of the spins that is spatially variable within the imaging volume. The flip angle is designed to be lower on a side or the imaging volume from which the liquid flows into the imaging volume than on the side at which the liquid flows out, and the flip angle increases monotonically.

15 Claims, 3 Drawing Sheets

(56) References Cited

OTHER PUBLICATIONS

Bi, et. al. "Non-Contrast-Enhanced Four-Dimensional (4D) Intracranial MR Angiography: A Feasibility Study" Magnetic Resonance in Medicine, vol. 63, pp. 835-841 (2010).
Edelman, et al. "Quiescent-Interval Single-Shot Unenhanced Magnetic Resonance Angiography of Peripheral Vascular Disease: Technical Considerations and Clinical Feasibility", Magn Reson Med., 2010; vol. 63; No. 4; pp. 951-958; (2010).
Le Roux, "Simplified model and stabilization of SSFP sequences" Journal of Magnetic Resonance, vol. 163, pp. 23-37; (2003).
Zur, "Optimized Slab Profile for 3D-TOF Angiography"; Proceedings of the Society of Magnetic Resonance in Medicine; vol. 2; p. 960; (1994).
Oppelt, et al. "FISP: eine neue schnelle Pulssequenz für die Kernspintomographie" electromedica, vol. 54, , Issue 1, pp. 15-18; (1986).

\* cited by examiner

MAGNETIC RESONANCE METHOD AND APPARATUS FOR IMAGING MOVING LIQUID IN A SUBJECT

BACKGROUND OF THE INVENTION

Field of the Invention

The present invention concerns a method for capturing magnetic resonance data from an imaging volume of a patient, in which liquid, in particular blood, is moving, by execution of a bSSFP magnetic resonance sequence, in which spins located within the imaging volume are excited cyclically (repeatedly) by radiation of a radio-frequency pulse, using a magnetic resonance scanner. The invention additionally concerns a magnetic resonance apparatus and to an electronically-readable data storage medium for implementing such a method.

Description of the Prior Art

A problem that often arises in clinical magnetic resonance imaging is the imaging of blood vessels or of the blood located therein. To this end, some options for capturing target imaging volumes/slices have already been proposed.

Magnetic resonance imaging methods are known in which non-equilibrium states are used to acquire magnetic resonance data. In this case, magnetization in a slice, in general thus in an imaging volume, is not constant while the raw data for the image are being acquired, but rather is ultimately "used up" during acquisition. As image coding progresses, the coded magnetic resonance signal becomes increasingly saturated, until an equilibrium state value is reached that is typical of the imaging technique. The rate at which the magnetic resonance signal decays toward the equilibrium state (hereinafter decay rate) depends on the relaxation parameters and the imaging technique.

If, as in the case of moving blood, macroscopic spatial transport of material and thus magnetization is present during imaging, the saturation state roughly correlates to the spatial position. The highest magnetic resonance signal is obtained where the flow enters the slice, and the lowest magnetic resonance signal is obtained at the other side of the slice. The decay rate with regard to the equilibrium states may be established for various imaging techniques, for example for the FLASH imaging technique with T1>TR as a function of the flip angle per unit time (FLASH=Fast Low-Angle Shot). For the bSSFP imaging technique (Balanced Steady-State Free Precession–balanced imaging with free precession in the equilibrium state), the decay rate is a flip angle-dependent mixture of T1 and T2, as described, in the article by Patrick Le Roux, "Simplified model and stabilization of SSFP sequences", Journal of Magnetic Resonance 163 (2003), pp. 23 to 37.

The decay rate (often denoted R) is highly relevant if the goal of the imaging is to measure the moving material, specifically flowing blood, in order to image the blood vessels, since the rate of decay to the equilibrium state then determines for how long the moving material may be separated from the static background and how far it has moved. For magnetic resonance angiography, this therefore represents a limit of the extent to which an expanding vascular tree may be visualized.

bSSFP-based Time-of-Flight (TOF) acquisitions are particularly suitable for magnetic resonance scanner in which a low basic magnetic field is produced, since the standardized, gradient echo-based TOF measurement is disadvantageous with regard to signal-to-noise ratio (SNR). bSSFP imaging techniques benefit, however, from an elevated T2/T1 ratio of the blood, SAR reduction and improved homogeneity in terms of peak B1 field (radio-frequency field) and B0 field (main field). The more disadvantageous aspects of bSSFP imaging techniques are less relevant in the case of lower basic fields.

To minimize decay within the imaging volume, i.e. the slice, it has been proposed to subdivide the imaging volume into a number of sub-volumes ("slabs") of reduced thickness in the direction of flow of the liquid, but this reduces efficiency because each sub-volume requires a prescan to stabilize background contrast, and oversampling has to be performed for each slab, and the signal-to-noise ratio is reduced at least for the background tissue.

For a tissue to appear bright in the FLASH imaging technique, the flip angle and repetition time TR have to be selected such that the inverse of the rate of decay to the equilibrium state is greater than the T1 relaxation time of the tissue/liquid. In applications such as TOF imaging, this cannot be achieved for blood, because the flip angles necessary for sufficient background suppression result in an inverse decay rate that is less than the T1 relaxation time for blood. This means that the blood signal decays while the blood moves through the imaging volume. A typical example of such a case is with a flip angle of 15° and a TR of 25 ms, because the inverse of the decay rate is then 720 ms.

To address this problem it has been proposed, with regard to the FLASH imaging technique, to use radio-frequency pulses that generate a flip angle that varies (is non-constant or non-uniform) over the imaging volume. Such pulses are called ramp pulses or TONE ("Tilt-Optimized Nonsaturated Excitation") pulses. At the slice boundary, where the liquid, in particular the blood, flows into the imaging volume, a reduced flip angle is used. The flip angle typically varies in linear fashion over the imaging volume, until it reaches the maximum flip angle on the opposite side or slice boundary. The ramp pulses used are highly asymmetric over time, so as to reduce echo time and SAR. A lower flip angle on the inflow side results in a markedly longer time to reach the equilibrium state, and therefore in a lower decay rate. In the above example, it is possible, using ramp pulses and beginning with half the maximum flip angle on the inflow side, to achieve an inverse decay rate of 3340 ms, which is markedly greater than the T1 relaxation time of blood.

If the bSSFP imaging technique is to be used to image blood flow, methods are conventionally used that focus on the imaging of high flow velocities. The sequence is interrupted, for example, if the flow introduces nonsaturated material into the imaging volume, after which data from the imaging volume are rapidly acquired, while decay within the imaging volume is negligible. A two-dimensional example is the QISS technique, in which the sequence is stopped while the heart pushes fresh blood into the imaging volume. Reference can be made, for example, to the article by R. R. Edelman et al., "Quiescent-interval single-shot unenhanced magnetic resonance angiography of peripheral vascular disease: Technical considerations and clinical feasibility", Magnetic Resonance in Medicine 63 (2010), pages 951-958.

If blood with a slower flow is to be imaged, the flip angle may be reduced, so lowering the decay rate, by increasing the T1 fraction and lowering the T2 fraction, as T1>T2 conventionally applies. One example of dynamic, non-contrast agent-enhanced angiography using the bSSFP imaging technique with continuous acquire is described, for example, in an article by X. Bi et al., "Non-contrastenhanced four-dimensional (4D) intracranial MR angiography: a feasibility study", Magnetic Resonance in Medicine 63 (2010), pages 835-841.

A disadvantage of the known use of bSSFP imaging techniques for imaging moving liquid, in particular blood, is that, due to the different equilibrium states of the liquid transported in the imaging volume, a non-uniform contrast is produced or, due to excessive flip angle reduction, excessively large signal losses may occur along the imaging path.

SUMMARY OF THE INVENTION

An object of the invention is to provide a way of using the bSSFP imaging technique, which maximizes the visualized distance from the inflow side of the imaging volume while also allowing sufficient signal strength over the entire imaging volume.

The method according to the invention for capturing magnetic resonance data from an imaging volume, such as a slice of a patient, in which liquid, such as blood, is moving, by execution of a bSSFP magnetic resonance sequence, in which spins located within the imaging volume are cyclically (repeatedly) excited by radiation of a radio-frequency pulse, using a magnetic resonance scanner. In accordance with the invention, a ramp pulse is used as the radio-frequency pulse, the ramp pulse being symmetrical over time and establishing a flip angle of the nuclear spins that is spatially variable within the imaging volume, and the flip angle is designed to be lower on the inflow side, from which the liquid flows into the imaging volume, than on the outflow side, at which the liquid flows out of the imaging volume, and so as to increase monotonically from the inflow side to the outflow side.

According to the invention, continuous bSSFP image acquisition is implemented, in particular for rapid flow, by replacing the SINC radio-frequency pulse used conventionally in bSSFP magnetic resonance sequences by a ramp pulse (TONE pulse) optimized specifically for the bSSFP magnetic resonance sequence. As with the above-discussed FLASH magnetic resonance sequence, the flip angle profile ensures that the amplified magnetic resonance signals of inflowing liquid are maintained for a longer time by the decay rate to the equilibrium state being minimized at the boundary of the imaging volume where flow enters and the magnetic resonance signal being maximized on the other side or at the other boundary of the imaging volume, the outflow side. The underlying mechanism does not correspond to that of FLASH magnetic resonance imaging, but rather is dependent on the fact that the T1 relaxation time is greater than the T2 relaxation time, which is correct in the case of blood as described above.

The ramp pulse is preferably designed to be symmetrical over time, because this improves integration into the balanced gradient diagram of the bSSFP magnetic resonance sequence and therefore does not introduce any additional moments. The symmetrical configuration of the ramp pulse has the further advantage of minimizing phase drift across the imaging volume, which would be disadvantageous for the equilibrium state magnetic resonance signal of fast-flowing material, as subsequent radio-frequency pulses (i.e. ramp pulses) would influence the fast-flowing spins at various positions, therefore with different phases.

Overall, therefore, the bSSFP magnetic resonance technique is optimized by using adapted ramp pulses (TONE pulses), which is particularly suitable for 3D-TOF-like applications. Enabling use of the bSSFP magnetic resonance sequence instead of the FLASH magnetic resonance sequence for TOF applications results in a markedly higher signal-to-noise ratio and faster coding times due to shorter repetition times (TR), thereby enabling non-contrast agent-enhanced angiography suitable for clinical applications in particular also on magnetic resonance devices with a low basic field.

In an embodiment, the monotonically increasing flip angle profile within the imaging volume is designed so as to homogenize the magnetic resonance data of the liquid within the imaging volume and/or to increase in linear manner from the inflow side to the outflow side. If the flow velocity through the imaging volume (the slice) is known, suitable decay rates and therefore flip angles may be determined, which may be taken as the basis for the ramp pulse as flip angle profile. As described above, the corresponding inter-relationships are known from the prior art or may be established experimentally and/or theoretically. This configuration allows an improved appearance for magnetic resonance images derived from acquired magnetic resonance data. The flip angle profile preferably increases monotonically and without jumps, i.e. smoothly, from the boundary on the inflow side to the boundary on the outflow side. In this case, a conventional, linear ramp may be selected, however other suitable flip angle profiles are also possible, for example nonlinear, in particular concave, profiles, for example square profiles.

It is expedient for the parameter that is taken into account with regard to the design of the ramp pulse to be a maximum load rating of the radio-frequency amplifier of the magnetic resonance device and/or with regard to the design of the overall acquire process to be an SAR limit value to be observed. The bSSFP imaging technique conventionally requires higher flip angles, for example in the range from 50° to 70°, such that it should be checked whether SAR limit values and/or the maximum load rating capacity of radio-frequency amplifiers are observed. SAR efficiency should thus be kept sufficiently low as far as power integrals/amplitude integrals are concerned, while at the same time the maximum necessary B1 field is to be kept small enough for it be possible to provide it through the radio-frequency amplifier.

In another embodiment of the present invention, a maximum gradient of the flip angle adjacent to the boundary of the slice forming the inflow side is restricted by a limit value dependent on the repetition time and flow velocity of the liquid. The product of the flow velocity of the liquid, the repetition time and the maximum gradient (flip angle gradient (slope)) may be selected to be smaller than the maximum flip angle value to be established and/or smaller than a fixed limit value in a range of from 1.5° to 15°, for example 10°. It is particularly convenient in this context for the flip angle profile on the inflow side to start outside the slice at a starting value of less than 5°, in particular 0°, and to increase in a linear manner as far as the outflow side of the slice, in particular using a constant gradient. The thought behind this is that no major jumps as far as the flip angle is concerned should occur in the bSSFP magnetic resonance sequence between spatially or chronologically adjacent spins. The flip angle profile starting close to zero as early as outside the imaging volume, and not increasing too rapidly, acts as a type of equilibrium catalyst for inflowing liquid, in particular inflowing blood. The initial ramping up gradient on the inflow side is dependent on the maximum expected flow velocity. The spins of the inflowing liquid are thus already appropriately prepared prior to entry into the imaging volume to be able to deliver the suitable signal.

In general, the ramp formed by the flip angle profile from the boundary of the imaging volume on the inflow side to the boundary of the imaging volume on the outflow side may cover over 10%, for example 50%, of the nominal flip angle which is achieved at the boundary on the outflow side for somewhat slow flow velocities, as is often also the case with FLASH magnetic resonance sequences. To this end, as just described, it is expedient for the initial ramping up outside the imaging volume (i.e. in an oversampling region) to be sufficiently shallow for the desired imaging properties to be achieved for the bSSFP magnetic resonance sequence. For high flow velocities, it has become apparent that a deviation from a linear flip angle profile toward a concave shape, for example a square ramp, may be advantageous for achieving robust imaging properties.

The pulse profile of the ramp pulse over time, as is known, may be determined by Fourier transformation of the specified flip angle profile in the frequency domain. A method for determining the ramp pulse may therefore include initially determining or specifying a true-value flip angle profile in the frequency space, wherein here flip angle profiles, for example, may be determined experimentally by measurements at different flow velocities and/or mathematical interrelationships derived from experiments and/or theoretical calculations may be used. The flip angle profile is then Fourier-transformed into the time domain in order to obtain a complex-value raw pulse shape.

In another embodiment of the invention the pulse profile is smoothed by application of a low-pass filter, in particular a Hanning filter. The final pulse shape with a limited number of sampling points may then be established by application of a low-pass filter to the raw pulse shape in the time domain, such as by application of a Hanning filter.

In addition to the method, the invention also concerns a magnetic resonance apparatus having a control computer configured to operate a scanner as to execute the method according to the invention. All explanations with regard to the method according to the invention apply analogously to the magnetic resonance apparatus according to the invention, with which the advantages described above can therefore likewise be obtained. In addition to the sequence controller conventionally provided in magnetic resonance devices, which coordinates progression of the magnetic resonance sequence by driving the components of the magnetic resonance scanner, such a controller can include a pulse determining processor that determines a ramp pulse, as described, when at least an estimate of the flow velocity of the liquid (blood) is available.

The present invention also encompasses a non-transitory, computer-readable data storage medium encoded with programming instructions that, when the storage medium is loaded into a computer or computer system of a magnetic resonance apparatus, cause the computer or computer system to operate the magnetic resonance apparatus in order to implement any or all embodiments of the method according to the invention, as described above.

The data storage medium may be a CD-ROM.

DESCRIPTION OF THE PREFERRED EMBODIMENTS

If three-dimensional TOF imaging of flowing blood is to proceed in an imaging volume, for example a slice, in a target area of a patient, for example for magnetic resonance angiography, in exemplary embodiments of the present invention a bSSFP magnetic resonance sequence is used which uses known regular radio-frequency pulses to bring the spins moving in phase in the imaging volume into an equilibrium state (steady state) over time. Instead of a SINC radio-frequency pulse, it is proposed to use a ramp pulse as radio-frequency pulse, in order to achieve a lower rate of decay to the equilibrium state on the inflow side by using lower flip angles while nevertheless maintaining a sufficiently high signal on the outflow side.

Figure 1:
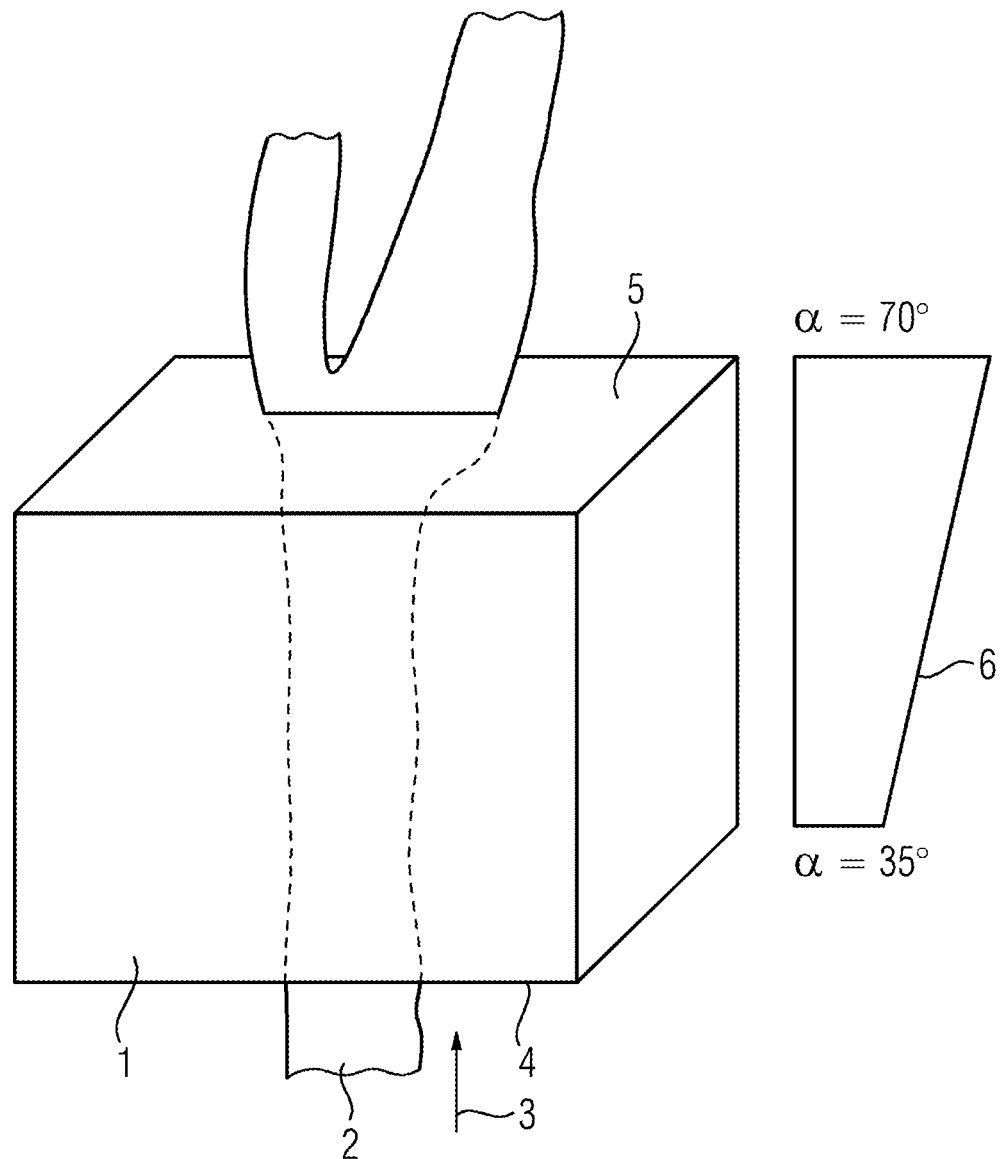
FIG. 1 shows an imaging volume through which a blood vessel flows, with a flip angle profile.

FIG. 1 illustrates this in more detail in the form of a simplified schematic diagram of a three-dimensional imaging volume 1, through which a blood vessel 2 extends. The arrow 3 here symbolizes the direction of flow, such that the imaging volume 1 has an inflow side 4 and an outflow side 5.

The box 6 indicates the flip angle profile within the imaging volume 1 from the boundary of the imaging volume 1 on the inflow side 4 to the boundary of the imaging volume 1 on the outflow side 5. The nominal flip angle value of the bSSFP magnetic resonance sequence is in this case 70°, but the initial flip angle on the inflow side 4 is 35°. The ramp pulse is configured such that the flip angle increases in linear manner until it reaches 70° at the boundary of the outflow side 5. It is thus ensured that the decay rate to the equilibrium state is smaller for spins of the blood entering the imaging volume 1, and it therefore takes longer until these spins reach the equilibrium state, such that they deliver an increased magnetic resonance signal in particular throughout their path through the imaging volume 1, which, for example, ensures clear visibility of the blood vessel 2. The increasing flip angle toward the outflow side 5 ensures that sufficient signal strength is present there.

The example shown in FIG. 1 is suitable for slow blood flow, while it is also conceivable, for strong blood flow with high flow velocities, to use other boundary values for the flip angle or other, preferably concave, profile shapes, in particular concave, for example square, profiles.

Figure 2:
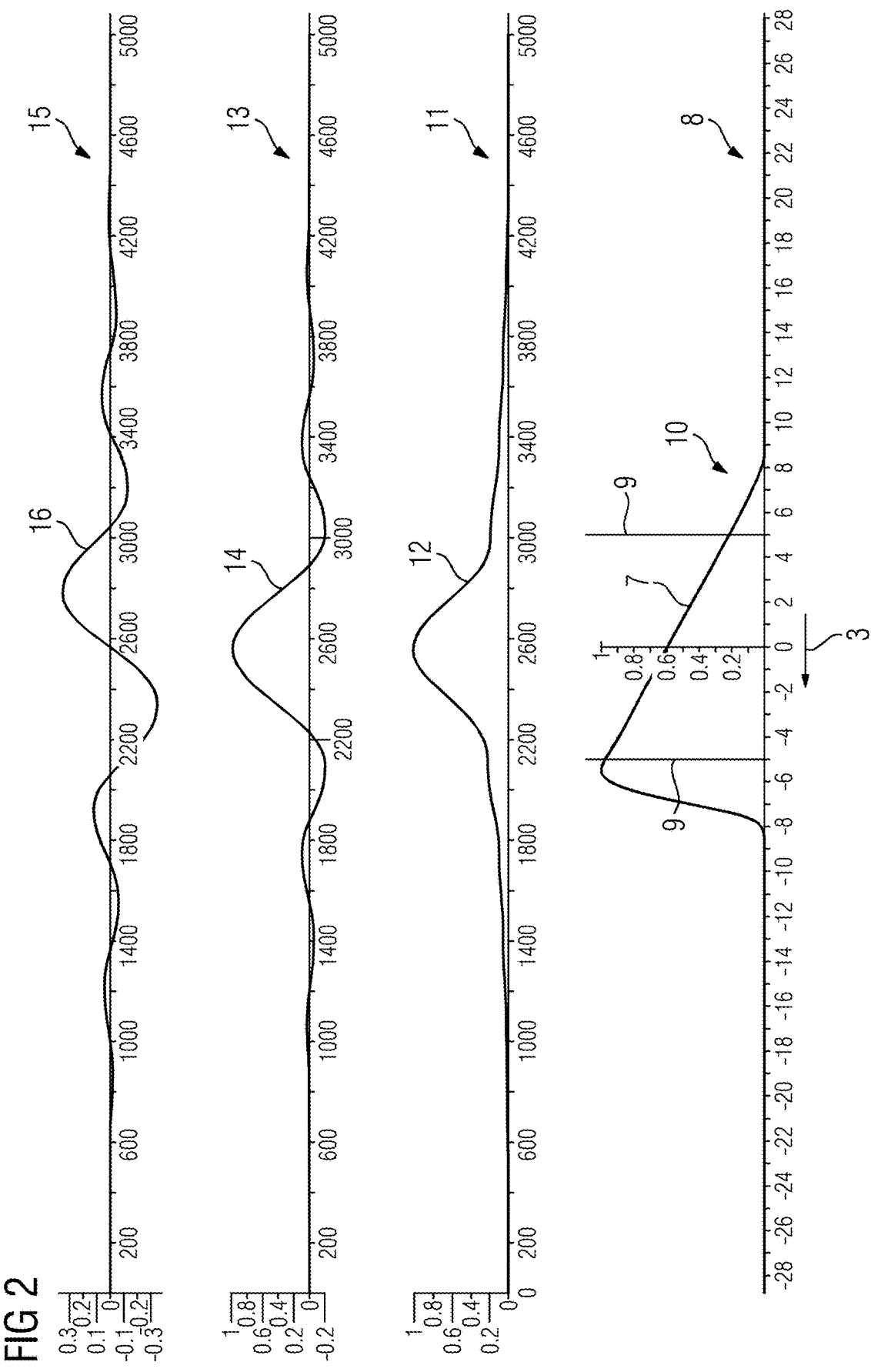
FIG. 2 shows graphs relating to the configuration and determination of a ramp pulse for a bSSFP magnetic resonance sequence.

FIG. 2 uses multiple graphs to show an initial flip angle profile and the resultant pulse shape (pulse profile over time) of a ramp pulse, as an example. The starting point for determining a suitable ramp pulse is a flip angle profile 7 to be defined in the frequency space, cf. graph 8. The lines 9 indicate the boundary of the imaging volume 1 in the frequency space. A linear, monotonically increasing, smooth profile of the flip angle from the inflow side 4 to the outflow side 5 is clearly provided within the imaging volume 1, said profile falling back to zero as quickly as the limitations, for example the SAR limit value, allow, once it has reached the boundary of the outflow side. The flip angle profile 7 within the imaging volume 1 is selected, as a function of the flow velocity based on experimental data and/or theoretical considerations/simulations, such that the increased magnetic resonance signals are maintained for the inflowing blood as far as possible over the entire imaging volume 1, the rate of decay to the equilibrium state therefore being sufficiently low, while maximally uniform homogeneity in the direction of flow 3 is achieved over the imaging volume 1.

Once the frequency limit 9 of the imaging volume has been exceeded on the inflow side 4, the linear profile is clearly continued in a portion 10 outside the imaging volume 1 down to the flip angle value 0°. In this way, it is ensured that a maximum gradient of the flip angle (flip angle gradient) is not exceeded. This maximum admissible gradient is here selected such that the product of the flow velocity of the blood, the repetition time and this maximum gradient in the portion 10 is markedly lower than the nominal flip angle value or indeed is lower than 10°. In this way, it is ensured that there is no excessively marked flip angle difference between the spins in the blood, so assisting in correct functioning of the bSSFP magnetic resonance sequence and allowing high image quality. The profile in the portion 10 therefore acts as a type of equilibrium state catalyst for inflowing blood.

In order then to obtain from the flip angle profile 7 the pulse shapes of the ramp pulse in the time domain, a Fourier transformation is undertaken, according to which a low-pass filter, here a Hanning filter, is additionally applied to the raw pulse shapes after Fourier transformation. Graph 11 shows in this respect the absolute fraction 12 of the pulse shape in the time domain, while graph 13 shows the imaginary fraction 14 of the pulse shape in the time domain and graph 15 shows the real fraction 16 of the pulse shape in the time domain. The pulse shape was here deliberately selected to be symmetrical to allow use in the bSSFP magnetic resonance sequence.

The bSSFP magnetic resonance sequence modified in this way may be used particularly advantageously for capturing 3D-TOF magnetic resonance data.

Figure 3:
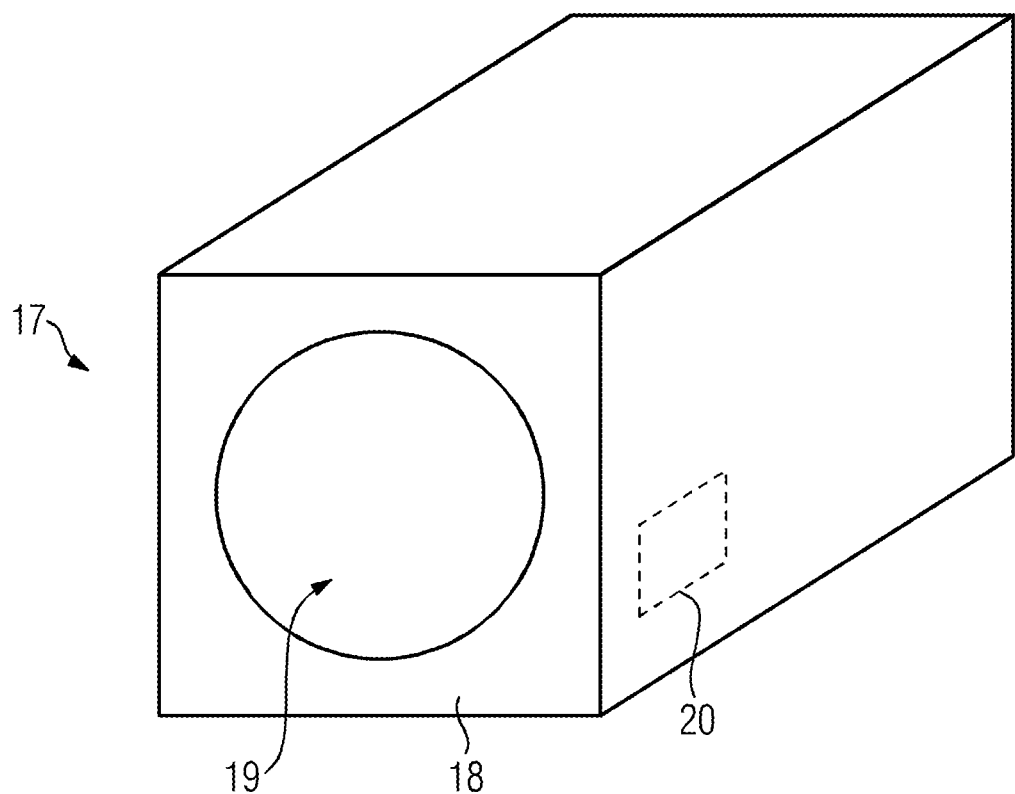
FIG. 3 schematically illustrates a magnetic resonance device according to the invention.

Finally, FIG. 3 shows a schematic diagram of a magnetic resonance apparatus 17 according to the invention which, as known in principle, has a scanner 18 with a patient accommodation space 19, into which a patient to be investigated can be introduced. A radio-frequency coil arrangement and a gradient coil arrangement may, as is known, be provided to surround the patient accommodation space 19. These and other components of the magnetic resonance device 17 are driven by a controller 20 of the magnetic resonance apparatus 17, which may therefore have a sequence controller for controlling these components so as to carry out a bSSFP magnetic resonance sequence as described. Furthermore, a ramp pulse determining processor may be provided, in order, as described, to derive ramp pulses from a flip angle profile 7 which has been specified or is even yet to be determined, which pulses may then be used as radio-frequency pulses of the bSSFP magnetic resonance sequence to be output regularly.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a magnetic resonance (MR) image of a moving liquid in an imaging volume of subject, said method comprising:
    in a computer, generating control signals for a bSSFP (balanced steady-state free precession) MR sequence in order to operate the MR data acquisition scanner with said bSSFP MR sequence, so as to cyclically excite nuclear spins in an imaging volume of a subject by cyclically radiating a radio-frequency pulse;
    in said computer, generating said control signals so as to design said radio-frequency pulse as a ramp pulse that is symmetrical with respect to time and that establishes a flip angle of said spins that spatially varies within said imaging volume, with said flip angle being lower at an inflow side of said imaging volume from which liquid, containing said nuclear spins, flows into said imaging volume, than at an outflow side of said imaging volume at which said liquid flows out of said imaging volume, and with said flip angle increasing monotonically between said inflow side and said outflow side; and
    from said computer, operating said MR data acquisition scanner so as to execute said bSSFP sequence with said ramp pulse, in order to acquire MR raw data from the nuclear spins in said liquid and, in said computer, reconstructing image data from said raw MR data and displaying said image data at a display screen so as to present a visualization of said liquid in said imaging volume.

2. A method as claimed in claim 1 comprising, in said computer, generating said control signals so as to give said flip angle a flip angle profile in said imaging volume that homogenizes said MR data of said liquid within said imaging volume.

3. A method as claimed in claim 1 comprising generating said control signals in said computer so as to give said flip angle a flip angle profile that increases linearly from said inflow side to said outflow side of said imaging volume.

4. A method as claimed in claim 1 wherein said MR data acquisition scanner comprises a radio-frequency amplifier that is used to radiate said radio-frequency pulse as said ramp pulse, and wherein said method comprises, in said computer, generating said control signals so as to design said ramp pulse dependent on a maximum load rating of said radio-frequency amplifier.

5. A method as claimed in claim 1 comprising generating said control signals in said computer so as to give said ramp pulse a design that causes an SAR (specific absorption rate) limit value not to be exceeded during execution of said bSSFP MR sequence.

6. A method as claimed in claim 1 comprising generating said control signals in said computer so as to restrict a maximum gradient of said flip angle, adjacent to a boundary of said imaging volume at said inflow side, so as to not exceed a limit value that is dependent on a repetition time of radiation of said ramp pulse and a flow velocity of said liquid.

7. A method as claimed in claim 6 comprising generating said control signals in said computer so that a product of said maximum gradient, said flow velocity, and said repetition time is less than said limit value.

8. A method as claimed in claim 7 wherein said limit value is in a range from 1.5° to 15°.

9. A method as claimed in claim 7 comprising generating said control signals in said computer to give said flip angle a flip angle profile that starts, outside and adjacent to said inflow side of said imaging volume, with a starting value of less than 5°, and increases linearly to said outflow side of said imaging volume.

10. A method as claimed in claim 9 wherein said flip angle profile increases linearly in said imaging volume with a constant gradient.

11. A method as claimed in claim 1 comprising generating said control signals in said computer to give said ramp pulse a pulse profile with respect to time that is determined by Fourier transformation of said flip angle profile in the frequency domain.

12. A method as claimed in claim 11 comprising generating said control signals in said computer so as to smooth said pulse profile of said ramp pulse with low-pass filtering.

13. A method as claimed in claim 12 comprising implementing said low-pass filtering with a Hanning filter.

14. A magnetic resonance (MR) apparatus comprising:
an MR data acquisition scanner comprising a radio-frequency radiator; and
a computer configured to:
generate control signals for a bSSFP (balanced steady-state free precession) MR sequence, in order to operate the MR data acquisition scanner with said bSSFP MR sequence, so as to cyclically excite nuclear spins in an imaging volume of a subject by cyclically radiating a radio-frequency pulse from said radio-frequency radiator;
generate said control signals so as to design said radio-frequency pulse as a ramp pulse that is symmetrical with respect to time and that establishes a flip angle of said spins that spatially varies within said imaging volume, with said flip angle being lower at an inflow side of said imaging volume from which liquid, containing said nuclear spins, flows into said imaging volume, than at an outflow side of said imaging volume at which said liquid flows out of said imaging volume, and with said flip angle increasing monotonically between said inflow side and said outflow side; and
operate said MR data acquisition scanner so as to execute said bSSFP sequence with said ramp pulse, in order to acquire MR raw data from the nuclear spins in said liquid, and to reconstruct image data from said raw MR data and display said image data at a display screen so as to present a visualization of said liquid in said imaging volume.

15. A non-transitory, computer-readable data storage medium encoded with programming instructions, said storage medium being loaded into a computer of a magnetic resonance (MR) apparatus that comprises an MR data acquisition scanner, said programming instructions causing said computer to:
generate control signals for a bSSFP (balanced steady-state free precession) MR sequence in order to operate the MR data acquisition scanner with said bSSFP MR sequence, so as to cyclically excite nuclear spins in an imaging volume of a subject by cyclically radiating a radio-frequency pulse;
generate said control signals so as to design said radio-frequency pulse as a ramp pulse that is symmetrical with respect to time and that establishes a flip angle of said spins that spatially varies within said imaging volume, with said flip angle being lower at an inflow side of said imaging volume from which liquid, containing said nuclear spins, flows into said imaging volume, than at an outflow side of said imaging volume at which said liquid flows out of said imaging volume, and with said flip angle increasing monotonically between said inflow side and said outflow side; and
operate said MR data acquisition scanner so as to execute said bSSFP sequence with said ramp pulse, in order to acquire MR raw data from the nuclear spins in said liquid, and reconstruct image data from said raw MR data, and display said image data at a display screen so as to present a visualization of said liquid in said imaging volume.

* * * * *